United States Patent
Petersen et al.

(10) Patent No.: US 6,893,861 B1
(45) Date of Patent: May 17, 2005

(54) METHOD FOR PRODUCING TRIFLUORO-3(R)-HYDROXYBUTYRIC ACID DERIVATIVES

(75) Inventors: Michael Petersen, Visp (CH); Olwen Birch, Visp (CH); Sakayu Shimizu, Kyoto (JP); Andreas Kjener, Visp (CH); Marie-Luise Hischier, Visp (CH); Susanne Thöni, Naters (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 09/622,385

(22) PCT Filed: Feb. 18, 1999

(86) PCT No.: PCT/EP99/01017
§ 371 (c)(1),
(2), (4) Date: Nov. 6, 2000

(87) PCT Pub. No.: WO99/42590
PCT Pub. Date: Aug. 26, 1999

(30) Foreign Application Priority Data

Feb. 18, 1998 (CH) .............................................. 388/98

(51) Int. Cl.$^7$ .............................. C12P 7/40; C12P 7/62
(52) U.S. Cl. ...................... 435/280; 435/134; 435/148; 435/189; 435/320.1; 435/136; 435/155
(58) Field of Search ................................ 435/280, 134, 435/148, 189, 320.1, 136, 155

(56) References Cited

U.S. PATENT DOCUMENTS 5,523,223 A * 6/1996 Kula et al. .................. 435/189

FOREIGN PATENT DOCUMENTS

EP 000736606 A1 * 10/1996

OTHER PUBLICATIONS

Kita et al., Appl. Environm. Microbiol., 63:2303–2310.*

* cited by examiner

*Primary Examiner*—Irene Marx
(74) *Attorney, Agent, or Firm*—Baker Botts LLP

(57) ABSTRACT

The invention relates to a biotechnological method for producing trifluoro-3(R)-hydroxybutyric acid derivatives of the general formula (I), where $R^1$ represents —$OR^2$, where $R^2$ is hydrogen, $C_{1-10}$ alkyl, $C_{1-10}$ alkenyl, $C_{3-8}$ cy-cloalkyl, aryl, alkoxyalkyl or alkoxyalkoxyalkyl; —$NR^3R^4$, where $R^3$ and $R^4$ are the same or different and represent hydrogen, $C_{1-10}$ alkyl, $C_{1-10}$ alkenyl, $C_{3-8}$ cycloalkyl or aryl; or —$SR^5$, where $R^5$ represents hydrogen, $C_{1-10}$ alkyl, $C_{1-10}$ alkenyl, aryl or $C_{3-8}$ cycloalkyl, based on a trifluoroacetoacetic acid derivative of the general formula (II), where $R^1$ has the meaning given above, by means of micro-organisms which are able to reduce a carbonyl function or by means of a cell-free enzyme extract of said micro-organisms.

9 Claims, 1 Drawing Sheet

METHOD FOR PRODUCING TRIFLUORO-3 (R)-HYDROXYBUTYRIC ACID DERIVATIVES

This application was filed under 35 U.S.C. 371 as the national phase of PCT/EP99/01017 filed Feb. 18, 1999.

The invention relates to a novel biotechnological process for preparing 4,4,4-trifluoro-3(R)-hydroxybutyric acid derivatives of the general formula

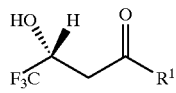
I 4,4,4-trifluoro-3(R)-hydroxybutyric acid derivatives such as ethyl 4,4,4-trifluoro-3(R)-hydroxybutyrate are important intermediates for preparing Befloxatone, a monomine oxidase A inhibitor (EP-A-0 736 606).

Several biotechnological processes for preparing 4,4,4-trifluoro-3(R)-hydroxybutyric esters have already been disclosed.

Guerrero, A. & Raja, E. (Bioorganic Chemistry Letters 1(12), 675–678) describe a microbiological process for preparing ethyl 4,4,4-trifluoro-3(R)-hydroxybutyrate using *Saccharomyces cerevisae* and proceeding from the corresponding racemate. In this method, the enantiomeric purity of the resulting desired product is poor.

EP-A-0 736 606 describes a biotechnological process for preparing ethyl 4,4,4-trifluoro-3(R)-hydroxybutyrate which uses the lipase Novozym 435 and which proceeds from ethyl 4,4,4-trifluoro-3-hydroxybutyrate. The disadvantage of this process is the indifferent yield of the desired product.

EP-A-0 577 446 includes a biotechnological process for preparing optically active ethyl 4,4,4-trifluoro-3-hydroxybutyrate which uses lipases and proceeds from the corresponding racemic ester. When this process is used, the product is obtained in low yield and its optical purity is poor.

WO 89/02 470 describes a process for preparing ethyl 4,4,4-trifluoro-3(R)-hydroxybutyrate which uses hydrolytic enzymes and which proceeds from racemic ethyl 4,4,4-trifluoro-3-acyloxybutyrate. However, this process does not yield the corresponding product in enantiomerically pure form.

The object of the present invention was to make available a biotechnological process for preparing 4,4,4-trifluoro-3 (R)-hydroxybutyric acid derivatives which enables the desired product to be isolated in good yield and at a good level of optical purity.

This object is achieved using the process according to claim 1.

According to the invention, the process is carried out by a trifluoroacetoacetic acid derivative of the general formula

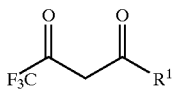
II in which
R1 is —$OR^2$, in which $R^2$ is hydrogen, $C_{1-10}$-alkyl, $C_{2-10}$-alkenyl, $C_{3-8}$-cycloalkyl, aryl, alkoxyalkyl or alkoxyalkoxyalkyl,
—$NR^3R^4$, in which $R^3$ and $R^4$ are identical or different and represent hydrogen, $C_{1-10}$-alkyl $C_{2-10}$-alkyl, $C_{2-10}$-alkenyl, $C_{3-8}$-cycloalkyl or aryl,
—$SR^5$, in which $R^5$ is hydrogen, $C_{1-10}$-alkyl, $C_{2-10}$-alkenyl, aryl or $C_{3-8}$-cycloalkyl, being converted by means of microorganisms which are able to reduce a carbonyl function, or by means of a cell-free enzyme extract of these microorganisms, into the compound of the general formula

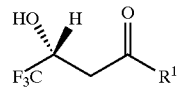
I in which $R^1$ has the same meaning.

In that which follows, a branched or unbranched, primary, secondary or tertiary aliphatic group, such as methyl, ethyl, propyl, isopropyl, butyl, isobutyl, sec-butyl, tert-butyl, pentyl, isopentyl, sec-pentyl, hexyl, heptyl, octyl, nonyl or decyl can be used as $C_{1-10}$-alkyl. $C_{1-10}$-alkyl preferably denotes ethyl, propyl, isopropyl or hexyl.

Ethenyl, propenyl, allyl, and butenyl can, for example, be used as $C_{2-10}$-alkenyl. Allyl is preferably used.

Aryl preferably denotes substituted or unsubstituted benzyl, phenyl or naphthyl. Halogenated benzyl, such as chloro- or bromobenzyl, can, for example, be used as substituted benzyl. Unsubstituted benzyl is preferably employed.

$C_{3-8}$-cycloalkyl preferably denotes cyclopropyl, cyclobutyl, cyclopentyl, cyclohexyl, cycloheptyl or cyclooctyl, preferably cyclohexyl.

Alkoxyalkyl preferably denotes $C_{1-6}$-alkoxyethyl such as methoxyethyl and ethoxyethyl, particularly preferably ethoxyethyl.

Alkoxyalkoxyalkyl preferably denotes 2-(2-$C_{1-6}$-alkoxyethoxy)ethyl, such as 2-(2-methoxy-ethoxy)ethyl and 2-(2-ethoxyethoxy)ethyl, with the latter being particularly preferably employed.

Consequently, preferred starting compounds are ethyl trifluoroacetoacetate, propyl trifluoroacetoacetate, isopropyl trifluoroacetoacetate and hexyl trifluoroacetoacetate, cyclohexyl trifluoroacetoacetate, benzyl trifluoroacetoacetate, ethoxyethyl trifluoroacetoacetate and ethoxyethoxyethyl trifluoroacetoacetate.

Examples of expedient microorganisms which are able to reduce a carbonyl function are microorganisms which contain an expressable gene for an enzyme which is able to reduce a carbonyl function, for example an enzyme possessing reductase activity, in particular a gene for an aldehyde reductase, an alcohol dehydrogenase or a ketone reductase. The enzymes which are able to reduce a carbonyl function can be NADPH (β-nicotinamide adenine dinucleotide phosphate)-dependent or be dependent on other cofactors. Preference is given to using microorganisms which contain NADPH-dependent reduction systems.

Cell-free enzyme extracts of these microorganisms can be obtained by means of methods which are customary to the skilled person, for example by means of the French press method, the ultrasonication method or the lysozyme method.

The biotransformation is expediently carried out using microrganisms which contain an aldehyde reductase, in particular an NADPH-dependent aldehyde reductase.

Microorganisms which contain an NADPH-dependent aldehyde reductase, such as microorganisms of the species *Sporobolomyces salmonicolor*, have already been described by Shimizu et al., 1990, Applied and Environmental Microbiology, 56(8), 2374–2377 and Kataoka, M. et al., Biochimica et Biophysica Acta, 1112, 57–62 (1992). These microorganisms can, on the one hand, be used themselves for the process according to the invention and, on the other hand, serve as the starting material for constructing plasmids and other suitable microorganisms.

Recombinant microorganisms which are transformed with a gene encoding an enzyme which is able to reduce a carbonyl function are expediently employed for the biotransformation. Examples of microorganisms which can be transformed with such a gene are microorganisms of the genus *Escherichia*, in particular the species *Escherichia coli*, for example *Escherichia coli* JM109, *Escherichia coli* DH5 and *Escherichia coli* HB101.

The gene possessing the reductase activity, for example an aldehyde reductase, is preferably located on a vector which is suitable for the transformation, for example a plasmid, expediently together with a promoter which is suitable for expressing the gene, such as the tac promoter ($P_{tac}$).

Provided the microorganisms employed contain NADPH-dependent enzymes, the biotransformation is expediently carried out in the presence of NADPH. The NADPH is either added directly in the requisite quantities or produced in situ. Advantageously, the NADPH is produced in situ. For this purpose, the biotransformation is expediently carried out in the presence of an NADPH generator or regenerator, i.e. an enzyme which catalyzes the formation of NADPH from its oxidized form, i.e. $NADP^+$. A glucose dehydrogenase, for example *Bacillus megaterium* glucose dehydrogenase, is expediently employed as the NADPH generator or regenerator.

In order to generate NADPH during the biotransformation, the latter is expediently carried out in the presence of a microorganism which expresses the NADPH generator. Recombinant microorganisms which are transformed with the gene encoding the NADPH generator are, in particular, used for this purpose. In this case, the gene for the NADPH generator is located on a vector which is suitable for the transformation, for example a plasmid, expediently together with a promoter which is suitable for expressing the gene, such as the tac promoter ($P_{tac}$).

Different microorganisms, one of which is able to reduce the carbonyl function and one of which is able to form NADPH, can be employed for preparing the trifluoro-3(R)-hydroxybutyric acid derivatives of the general formula I using, in the presence of an NADPH generator, a microorganism which contains an NADPH-dependent enzyme which is capable of reducing a carbonyl function, for example an NADPH-dependent aldehyde reductase. However, the microorganisms which are used in accordance with the invention, and which are able to reduce a carbonyl function, advantageously already themselves contain a gene which encodes an NADPH generator or regenerator, for example a gene which encodes a glucose dehydrogenase.

Recombinant microorganisms which are transformed with a gene which encodes an NADPH-dependent enzyme, for example a gene which encodes an NADPH-dependent aldehyde reductase, and also a gene which encodes an NADPH generator or regenerator, for example a gene which encodes a glucose dehydrogenase, are advantageously employed for the biotransformation. In one possible embodiment, these genes are located for expression on one single plasmid. In another embodiment, these genes are present on different, mutually compatible plasmids.

Consequently, the biotransformation can advantageously be carried out using microorganisms which contain:
  at least one vector, for example a plasmid, which contains a gene for an enzyme which is capable of reducing a carbonyl function, for example an aldehyde reductase gene;
  at least two vectors, for example plasmids, one of which contains a gene for an enzyme capable of reducing a carbonyl function, for example an aldehyde reductase gene, while the other contains a gene for an NADPH generator or regenerator, for example a glucose dehydrogenase gene; or
  at least one vector, for example a plasmid, which contains both a gene for an enzyme which is capable of reducing a carbonyl function, for example an aldehyde reductase gene, and also a gene for an NADPH generator or regenerator, for example a glucose dehydrogenase gene.

Advantageously, the biotransformation is carried out using microorganisms of the species *E. coli* JM109 or *E. coli* DH5 which are transformed with at least two plasmids which respectively contain an aldehyde reductase gene and a glucose dehydrogenase gene, or using microorganisms of the species *E. coli* HB101 or *E. coli* DH5 which are transformed with at least one plasmid which contains both genes, i.e. the aldehyde reductase gene and the glucose dehydrogenase gene. In particular, the biotransformation is carried out using *E. coli* JM109 and *E. coli* DH5 which contain an aldehyde reductase gene and a glucose dehydrogenase gene. Naturally, the biotransformation can also be carried out using different microorganisms which in each case contain only one of the said genes.

Figure 1:
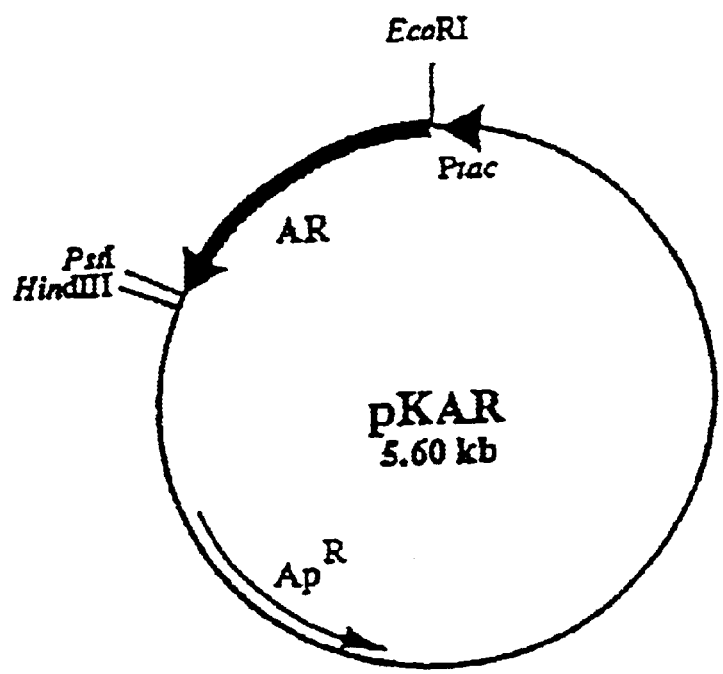
FIG. 1 shows the structure of a plasmid, pKAR, which is suitable for the present invention and which contains the gene for the *Sporobolomyces salmonicolor* NADPH-dependent aldehyde reductase together with the $P_{tac}$ promoter and an ampicillin (Ap) resistance as the selection marker.
Figure 2:
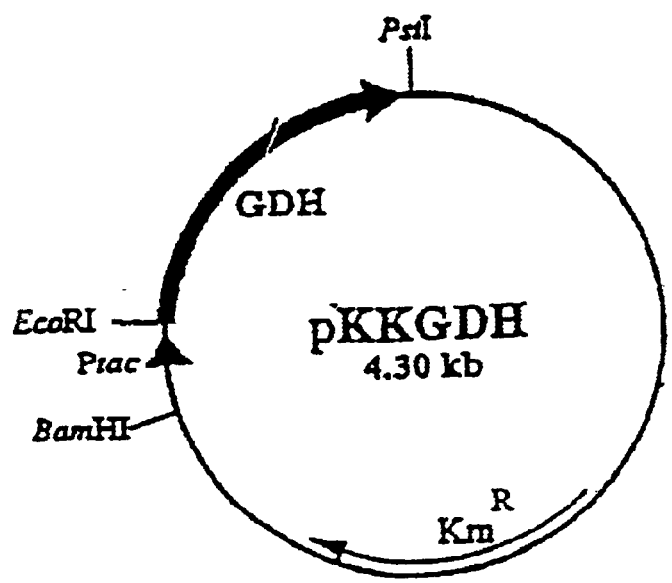
FIG. 2 shows the structure of another plasmid, pKKGDH, which is suitable for the present invention and which contains the gene for the *Bacillus megaterium* glucose dehydrogenase together with the $P_{tac}$ promoter and a kanamycin (Km) resistance as the selection marker.

The microorganism *E. coli* JM109, harbouring the plasmid pKAR, containing a gene encoding the *Sporobolomyces salmonicolor* NADPH-dependent aldehyde reductase, and the plasmid pKKGDH, containing a gene encoding the *Bacillus megaterium* glucose dehydrogenase, was deposited in the Deutsche Sammlung von Mikroorganismen and Zellkulturen [German Collection of Microorganisms and Cell Cultures] GmbH (DSMZ), D-38124 Braunschweig, Mascheroderweg 1b, Germany, under designation DSM 11902, in accordance with the Budapest Treaty, on 16 Dec. 1997. The microorganism *E. coli* DH5, harbouring the plasmids pKAR and pKKGDH, was deposited in the above-mentioned depository institution under designation DSM 12566, in accordance with the Budapest Treaty, on 7 Dec. 1998.

The genes can be expressed in dependence on the expression system. In the case of the expression systems which are preferably used in accordance with the invention, the expression of the genes can, for example, be induced with IPTG (isopropylthio-galactoside) if *E. coli* JM109 or *E. coli* HB101 is used as the microorganism. As the skilled person knows, induction with IPTG is not necessary when *E. coli* DH5 is used.

Following customary culture of the cells, the biotransformation can be carried out in a single-phase or two-phase system, preferably in a two-phase system.

Buffer media which are customary to the skilled person, such as low molecular weight phosphate buffers or Tris buffers, can be employed as a single-phase system.

The said buffer media which are customary to the skilled person, together with an organic solvent in which the starting compound is soluble, can be used as a two-phase system. Examples of suitable organic solvents are esters, alcohols, halogenated hydrocarbons, ethers, aliphatic $C_{5-12}$-hydrocarbons or aromatic hydrocarbons. Acetic esters, such as methyl acetate, ethyl acetate, propyl acetate and butyl acetate, can be used as esters. $C_{4-10}$-alcohols, such as hexanol, heptanol and octanol, can be used as alcohols.

Benzene, toluene and xylene can, for example, be used a aromatic hydrocarbons. Chloroform and dichloromethane can, for example, be used as halogenated hydrocarbons. Diethyl ether, tetrahydrofuran, methyl tert-butyl ether and dibutyl ether can, for example, be used as ethers. Examples of suitable aliphatic $C_{5-12}$-hydrocarbons are pentane, hexane, heptane, octane, nonane and decane.

A two-phase system in which the second phase consists of the starting compound and/or product is also suitable. Cosolvents can be employed for increasing the solubility of the starting compound. Either low molecular weight aliphatic alcohols, such as methanol, ethanol, propanol, isopropanol or tert-butanol, or inert solvents, such as dimethyl sulphoxide, acetone and acetonitrile, can be used as cosolvents.

The biotransformation is customarily carried out in the presence of a C source. Examples of suitable C sources are carbohydrates such as glucose, fructose or sucrose, and sugar alcohols, such as glycerol.

The pH of the media can be in a range of from 5 to 10, preferably of from 6 to 8.

The biotransformation is expediently carried out at a temperature of from 5 to 60° C., preferably of from 10 to 40° C.

After a reaction time of from a few minutes to 50 h, the desired product can then be isolated in high yield and at high enantiomeric purity (ee).

EXAMPLES

Example 1

Culturing the Microorganisms

E. coli JM109/pKAR,pKKGDH (DSMZ 11902) cells were cultured at 22° C. in 12 l of mineral salt medium (Table 1) in a 20 l fermenter. After 6 h, IPTG was added in order to induce the cells. Glycerol was then added and the cells were cultured, within 52 h, up to an optical density of $OD_{650nm}$=41.8. The cells were then stored at −80° C.

TABLE 1

| Yeast extract | 0.5 g/l |
| Glycerol | 30 g/l |
| $MgCl_2 \times 6H_2O$ | 0.8 g/l |
| $CaCl_2$ | 0.16 g/l |
| $(NH_4)_2SO_4$ | 2.0 g/l |
| SLF solution | 1.0 ml/l |
| Fe-EDTA solution | 1.5 ml/l |
| PPG-2000 | 0.1 g/l |
| $Na_2HPO_4 \times 2H_2O$ | 1.0 g/l |
| $KH_2PO_4$ | 1.0 g/l |
| $K_2HPO_4$ | 1.0 g/l |
| Thiamine | 10 mg/l |
| SLF solution: | |
| KOH | 15.1 g/l |
| $EDTA\ Na_2 \times 2H_2O$ | 100 g/l |
| $ZnSO_4 \times 7H_2O$ | 9.0 g/l |
| $MnCl_4 \times 4H_2O$ | 4.0 g/l |
| $H_3BO_3$ | 2.7 g/l |
| $CoCl_3 \times 6H_2O$ | 1.8 g/l |
| $CuCl_2 \times 2H_2O$ | 1.5 g/l |
| $NiCl_2 \times 6H_2O$ | 0.18 g/l |
| $Na_2MoO_4 \times 2H_2O$ | 0.27 g/l |
| Fe-EDTA solution: | |
| KOH | 10 g/l |
| $EDTANa_2 \times 2H_2O$ | 50 g/l |
| $FeSO_4 \times 7H_2O$ | 20 g/l |

Example 2

Preparation of Ethyl 4,4,4-Trifluoro-3(R)-Hydroxybutyrate a) 140 g of glucose and 0.56 g of NADP$^+$ were added to 800 ml of mineral salt medium (Table 1) containing E. coli JM109/pKAR,pKKGDH at an $OD_{650nm}$ of 7.2. 400 ml of butyl acetate containing 70 g of ethyl 4,4,4-trifluoroacetoacetate were added and the resulting mixture was placed in a 2 l fermenter, stirred at 400 rpm and gassed with air (400 ml/min). The pH was kept at 6.0 by adding 1 M $Na_2CO_3$. After 24 h, the organic phase contained 48 g of ethyl 4,4,4-trifluoro-3(R)-hydroxybutyrate having an ee value of >99%, corresponding to a molar yield of 67.8%.

b) 140 g of glucose and 0.56 g of NADP$^+$ were added to 800 ml of potassium phosphate buffer (100 mM, pH 6.0) containing the microorganisms according to Example 1 at an $OD_{650nm}$ of 30.7. 400 ml of butyl acetate containing 70 g of ethyl 4,4,4-trifluoroacetoacetate were added and the resulting mixture was fed into a fermenter as described in Example 2a. The pH was kept at pH 6.0 by adding 1 M $Na_2CO_3$. After 25 h, a further 10 g of ethyl 4,4,4-trifluoroacetoacetate were added. After 45 h, the organic phase contained 49 g of ethyl 4,4,4-trifluoro-3(R)-hydroxybutyrate having an ee value of >99%, corresponding to a molar yield of 60.6%.

c) 140 g of glucose and 50 mg of NAPD$^+$ were added to 800 ml of potassium phosphate buffer (0.1 M, pH 6.0) containing E. coli JM109/pKAR,pKKGDH at an $OD_{650nm}$ of 7.6. 400 ml of butyl acetate containing 70 g of ethyl 4,4,4-trifluoroacetoacetate were added and the resulting mixture was placed in a 2 l fermenter, stirred at 400 rpm and gassed with air (400 ml/min). The pH was kept at 6.0 by adding 1 M $Na_2CO_3$. A further 50 mg of NADP$^+$ were added 5 h after starting the fermenter. After 24 h, the organic phase contained 50 g of ethyl 4,4,4-trifluoro-3(R)-hydroxybutyrate having an ee value of >99.8%, corresponding to a molar yield of 71%.

d) 140 g of glucose and 50 mg of NAPD$^+$ were added to 800 ml of potassium phosphate buffer (0.1 M, pH 6.0) containing E. coli DH5/pKAR,pKKGDH at an $OD_{650nm}$ of 6.5. 400 ml of butyl acetate containing 70 g of ethyl 4,4,4-trifluoroacetoacetate were added and the resulting mixture was placed in a 2 l fermenter, stirred at 400 rpm and gassed with air (400 ml/min). The pH was kept at 6.0 by adding 1 M $Na_2CO_3$. A further 50 mg of NADP$^+$ were in each case added after 5 h and after 26 h. After 46 h, the organic phase contained 35 g of ethyl 4,4,4-trifluoro-3(R)-hydroxybutyrate having an ee value of >99.7%, corresponding to a molar yield of 51%.

Example 3

Preparation of Isopropyl 4,4,4-Trifluoro-3(R)-Hydroxybutyrate a) 140 g of glucose and 0.56 g of NADP$^+$ were added to 800 ml of mineral salt medium in accordance with Example 1 containing E. coli JM109/pKAR,pKKGDH at an $OD_{650nm}$ of 9.7. 400 ml of butyl acetate containing 70 g of isopropyl 4,4,4-trifluoroacetoacetate were added and the resulting mixture was fed into fermenter as described in Example 2. The pH was kept at pH 6.0 by adding 1 M $Na_2CO_3$. After 21 h, the organic phase contained 42.2 g of isopropyl 4,4,4-trifluoro-3(R)-hydroxybutyrate having an ee value of >99%, corresponding to a molar yield of 59.7%.

b) 140 g of glucose and 50 mg of NADP$^+$ were added to 800 ml of potassium phosphate buffer (0.1 M, pH 6.0) containing E. coli DH5/pKAR,pKKGDH at an $OD_{650nm}$ of 8.5. 400 ml of butyl acetate containing 70 g of isopropyl 4,4,4-trifluoroacetoacetate were added and the resulting mixture was placed in a 2 l fermenter, stirred at 400 rpm and gassed with air (400 ml/min). The pH was kept at 6.0 by adding 1 M $Na_2CO_3$. A further 50 mg of NADP$^+$ were added 5 h after starting the fermenter. After 24 h, the organic phase contained 32 g of isopropyl 4,4,4-trifluoro-3(R)- hydroxybutyrate having an ee value of >99.9%, corresponding to a molar yield of 46%.

Example 4
Preparation of Hexyl 4,4,4-Trifluoro-3(R)-Hydroxybutyrate 140 g of glucose and 50 mg of NADP$^+$ were added to 800 ml of potassium phosphate buffer (0.1 M, pH 6.0) containing *E. coli* DH5/pKAR,pKKGDH at an OD$_{650nm}$ of 9.5. 400 ml of butyl acetate containing 70 g of hexyl 4,4,4-trifluoroacetoacetate were added and the resulting mixture was placed in a 2 l fermenter, stirred at 400 rpm and gassed with air (400 ml/min). The pH was kept at pH 6.0 by adding 1 M Na$_2$CO$_3$. A further 50 mg of NAPD$^+$ were added 5 h after starting the fermenter. After 24 h, the organic phase contained 2 g of hexyl 4,4,4-trifluoro-3(R)-hydroxybutyrate having an ee value of >99.9%, corresponding to a molar yield of 3%.

Example 5
Preparation of Cyclohexyl 4,4,4-Trifluoro-3(R)-Hydroxybutyrate 140 g of glucose and 50 mg of NADP$^+$ were added to 800 ml of potassium phosphate buffer (0.1 M, pH 6.0) containing *E. coli* DH5/pKAR,pKKGDH at an OD$_{650nm}$ of 8.9. 400 ml of butyl acetate containing 70 g of cyclohexyl 4,4,4-trifluoroacetoacetate were added and the resulting mixture was placed in a 2 l fermenter, stirred at 400 rpm and gassed with air (400 ml/min). The pH was kept at pH 6.0 by adding 1 M Na$_2$CO$_3$. A further 50 mg of NAPD$^+$ were added 5 h after starting the fermenter. After 24 h, the organic phase contained 16 g of cyclohexyl 4,4,4-trifluoro-3(R)-hydroxybutyrate having an ee value of >99.9%, corresponding to a molar yield of 23%.

Example 6
Preparation of Benzyl 4,4,4-Trifluoro-3(R)-Hydroxybutyrate 140 g of glucose and 50 mg of NADP$^+$ were added to 800 ml of potassium phosphate buffer (0.1 M, pH 6.0) containing *E. coli* DH5/pKAR,pKKGDH at an OD$_{650nm}$ of 9.0. 400 ml of butyl acetate containing 70 g of benzyl 4,4,4-trifluoroacetoacetate were added and the resulting mixture was placed in a 2 l fermenter, stirred at 400 rpm and gassed with air (400 ml/min). The pH was kept at pH 6.0 by adding 1 M Na$_2$CO$_3$. A further 50 mg of NAPD$^+$ were added 5 h after starting the fermenter. After 24 h, the organic phase contained 6 g of benzyl 4,4,4-trifluoro-3(R)-hydroxybutyrate having an ee value of >99.9%, corresponding to a molar yield of 9%.

Example 7
Preparation of 2-Ethoxyethyl 4,4,4-Trifluoro-3(R)-Hydroxybutyrate 105 g of glucose and 37.5 mg of NADP$^+$ were added to 600 ml of potassium phosphate buffer (0.1 M, pH 6.0) containing *E. coli* DH5/pKAR,pKKGDH at an OD$_{650nm}$ of 10.2. 300 ml of butyl acetate containing 35 g of ethoxyethyl 4,4,4-trifluoroacetoacetate were added and the resulting mixture was placed in a 2 l fermenter, stirred at 400 rpm and gassed with air (300 ml/min). The pH was kept at pH 6.0 by adding 1 M Na$_2$CO$_3$. A further 37.5 mg of NAPD$^+$ were added 5 h after starting the fermenter. After 24 h, the organic phase contained 4 g of ethoxyethyl 4,4,4-trifluoro-3(R)-hydroxybutyrate having an ee value of 98.6%, corresponding to a molar yield of 12%.

Example 8
Preparation of 2-(2-Ethoxyethoxy)Ethyl 4,4,4-Trifluoro-3(R)-Hydroxybutyrate 105 g of glucose and 37.5 mg of NADP$^+$ were added to 600 ml of potassium phosphate buffer (0.1 M, pH 6.0) containing *E. coli* DH5/pKAR,pKKGDH at an OD$_{650nm}$ of 10.7. 300 ml of butyl acetate containing 35 g of ethoxyethoxyethyl 4,4,4-trifluoroacetoacetate were added and the resulting mixture was placed in a 2 l fermenter, stirred at 400 rpm and gassed with air (300 ml/min). The pH was kept at pH 6.0 by adding 1 M Na$_2$CO$_3$. A further 37.5 mg of NAPD$^+$ were added 5 h after starting the fermenter. After 24 h, the organic phase contained 5 g of ethoxyethoxyethyl 4,4,4-trifluoro-3(R)-hydroxybutyrate having an ee value of >99.9%, corresponding to a molar yield of 16%.

Example 9
Preparation of Methyl 4,4,4-Trifluoro-3(R)-Hydroxybutyrate 105 g of glucose and 37.5 mg of NADP$^+$ were added to 600 ml of potassium phosphate buffer (0.1 M, pH 6.0) containing *E. coli* DH5/pKAR,pKKGDH at an OD$_{650nm}$ of 11. 4. 300 ml of butyl acetate containing 33 g of methyl 4,4,4-trifluoroacetoacetate were added and the resulting mixture was placed in a 2 l fermenter, stirred at 400 rpm and gassed with air (300 ml/min). The pH was kept at pH 6.0 by adding 1 M Na$_2$CO$_3$. A further 37.5 mg of NAPD$^+$ were added 5 h after starting the fermenter. After 24 h, the organic phase contained 3.6 g of methyl 4,4,4-trifluoro-3(R)-hydroxybutyrate having an ee value of 96.1%, corresponding to a molar yield of 7%.

What is claimed is:

1. A process for preparing 4,4,4-trifluoro-3(R)-hydroxybutyric acid derivatives of the formula

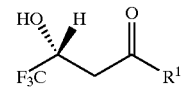

wherein R$^1$ is
- (a) —OR$^2$, in which R$^2$ is hydrogen, C$_{1-10}$-alkyl, C$_{2-10}$-alkenyl, C$_{3-8}$-cycloalkyl, aryl, alkoxyalkyl or alkoxyalkoxyalkyl,
- (b) —NR$^3$R$^4$, in which R$^3$ and R$^4$ are identical or different and represent hydrogen, C$_{1-10}$-alkyl, C$_{2-10}$-alkenyl, C$_{3-8}$-cycloalkyl or aryl, or
- (c) —SR$^5$, in which R$^5$ is hydrogen, C$_{1-10}$-alkyl, C$_{2-10}$-alkenyl, aryl or C$_{3-8}$-cycloalkyl, which process comprises:
(i) reacting a trifluoroacetoacetic acid derivative of formula II

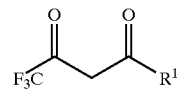

wherein R$^1$ is
- (a) —OR$^2$, in which R$^2$ is hydrogen, C$_{1-10}$-alkyl, C$_{2-10}$-alkenyl, C$_{3-8}$-cycloalkyl, aryl, alkoxyalkyl or alkoxyalkoxyalkyl,
- (b) —NR$^3$R$^4$, in which R$^3$ and R$^4$ are identical or different and represent hydrogen, C$_{1-10}$-alkyl, C$_{2-10}$-alkenyl, C$_{3-8}$-cycloalkyl or aryl, or
- (c) —SR$^5$, in which R$^5$ is hydrogen, C$_{1-10}$-alkyl, C$_{2-10}$-alkenyl, aryl or C$_{3-8}$-cycloalkyl, with a microorganism of the species *Escherichia coli* or cell-free extracts derived therefrom, wherein said microorganism is transformed with a gene encoding a NADPH generator or regenerator and wherein said microorganism expresses an NADPH-dependent enzyme having carbonyl reductase activity which enantioselectively reduces the trifluoroacetoacetic acid derivatives of formula II leading to the production of 4,4,4-trifluoro-3(R)-hydroxybutyric acid derivatives of the formula:

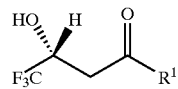

I wherein $R^1$ is (a) —$OR^2$, in which $R^2$ is hydrogen, $C_{1-10}$-alkyl, $C_{2-10}$-alkenyl, $C_{3-8}$-cycloalkyl, aryl, alkoxyalkyl or alkoxyalkoxyalkyl, (b) —$NR^3R^4$, in which $R^3$ and $R^4$ are identical or different and represent hydrogen, $C_{1-10}$-alkyl, $C_{2-10}$-alkenyl, $C_{3-8}$-cycloalkyl or aryl, or (c) —$SR^5$, in which $R^5$ is hydrogen, $C_{1-10}$-alkyl, $C_{2-10}$-alkenyl, aryl or $C_{3-8}$-cycloalkyl; and (ii) isolating the 4,4,4-trifluoro-3(R)-hydroxybutyric acid derivatives produced.

2. The process according to claim 1 wherein the *Escherichia coli* is selected from the group consisting of *Escherichia coli* JM109, *Escherichia coli* HB101 and *Escherichia coli* DH5.

3. The process according to claim 1 wherein the *Escherichia coli* is transformed with a gene encoding a glucose dehydrogenase.

4. The process of claim 3 wherein the *Escherichia coli* is transformed with the plasmids pKAR and pKKGDH, as deposited under the deposition numbers DSM 11902 and DSM 12566, respectively.

5. The process according to any one of claims 1, 2, or 4 wherein said process for preparing 4,4,4-trifluoro-3(R)-hydroxybutyric acid derivatives is carried out at a temperature of from 5 to 60° C.

6. The process of claim 3 wherein said process for preparing 4,4,4-trifluoro-3(R)-hydroxybutyric acid derivatives is carried out at a temperature of from 5 to 60° C.

7. The process according to one of claims 1, 2, or 4, wherein said process is carried out at a pH of from 5 to 10.

8. The process according to claim 3 wherein said process is carried out at a pH of from 5 to 10.

9. The process according to claim 1 wherein the NADPH-dependent enzyme is from expressing of a gene from *Sporobolomyces salmonicolor* as harbored on plasmid pKAR.

* * * * *